(12) United States Patent
Arns et al.

(10) Patent No.: US 10,835,746 B2
(45) Date of Patent: Nov. 17, 2020

(54) METHOD OF IDENTIFYING AND GUIDING CORTICAL STIMULATION SITES FOR THE APPLICATION OF A FOCAL-NEUROMODULATION TECHNIQUE

(71) Applicant: NEUROCARE GROUP NETHERLANDS B.V., Nijmegen (NL)

(72) Inventors: Martijn Wilco Arns, Nijmegen (NL); Arie Quirinus Bastiaan Brandwijk, Bilthoven (NL); Tabitha Amanda Iseger, Nijmegen (NL)

(73) Assignee: NEUROCARE GROUP NETHERLANDS B.V., Nijmegen (NL)

( * ) Notice: Subject to any disclaimer, the term of this patent is extended or adjusted under 35 U.S.C. 154(b) by 66 days.

(21) Appl. No.: 16/060,860

(22) PCT Filed: Dec. 9, 2016

(86) PCT No.: PCT/NL2016/050865
§ 371 (c)(1),
(2) Date: Jun. 8, 2018

(87) PCT Pub. No.: WO2017/099603
PCT Pub. Date: Jun. 15, 2017

(65) Prior Publication Data
US 2019/0001132 A1   Jan. 3, 2019

(30) Foreign Application Priority Data

Dec. 9, 2015 (NL) .................................. 2015931
Jun. 16, 2016 (NL) .................................. 2016974

(51) Int. Cl.
*A61N 2/00* (2006.01)
*A61N 1/36* (2006.01)
(Continued)

(52) U.S. Cl.
CPC ........ *A61N 1/36025* (2013.01); *A61B 5/0006* (2013.01); *A61B 5/02416* (2013.01); *A61N 2/006* (2013.01)

(58) Field of Classification Search
CPC .............. A61B 5/0006; A61B 5/02416; A61N 1/36025; A61N 2/006
See application file for complete search history.

(56) References Cited

U.S. PATENT DOCUMENTS

| | | |
|---|---|---|
| 2010/0324377 A1 | 12/2010 | Woehrle |
| 2013/0085316 A1 | 4/2013 | Fox et al. |
| 2015/0174418 A1* | 6/2015 | Tyler .................... A61B 5/055 601/2 |

FOREIGN PATENT DOCUMENTS

WO   2014145847 A1   9/2014

* cited by examiner

*Primary Examiner* — George Manuel
(74) *Attorney, Agent, or Firm* — AEON Law, PLLC; Adam L. K. Philipp; Jonathan E. Olson

(57) ABSTRACT

A method for identifying at least one cortical stimulation site in a subject for the application as a target that can be used for treatment of a psychiatric/neurological disorder related to a deep brain region of the ventromedial prefrontal cortex including the subgenual and rostral anterior cingulate by using a first focal-neuromodulation technique, said method comprising:
applying pulses of a second a focal-neuromodulation technique to different cortical areas of said subject;
simultaneously with the application of said pulses at a cortical area measuring a psychophysiological signal representative of a heart rate of the subject for said cortical area, and
when observing a systematic change in psychophysiological signal, identifying a corresponding cortical area as at least one cortical stimulation site that is functionally (Continued)

connected to said deep brain region of the ventromedial prefrontal cortex including the subgenual and rostral anterior cingulate for presenting said target for the treatment.

30 Claims, 1 Drawing Sheet

(51) Int. Cl.
*A61B 5/00* (2006.01)
*A61B 5/024* (2006.01)

METHOD OF IDENTIFYING AND GUIDING CORTICAL STIMULATION SITES FOR THE APPLICATION OF A FOCAL-NEUROMODULATION TECHNIQUE

FIELD OF THE INVENTION

The invention relates to identifying a cortical area for the application of a focal-neuromodulation technique, in particular by manipulating a deeper cortical or sub-cortical area.

BACKGROUND OF THE INVENTION

A method and system are described for using electromagnetic stimulation. In this way, for instance a cortical area can be identified. The cortical area identified in this way can subsequently be used for instance for therapeutic action of transcranial magnetic stimulation or TMS in for example depression.

Regarding magnetic brain stimulation in general, reference is made to the following publication, that will be further discussed below in the explanation of the current invention:

(1) Schutter, D. J. L. G.: Quantitative review of the efficacy of slow-frequency magnetic brain stimulation in major depressive disorder. Psychol. Med. 1-7 (2010);

(2) Schutter, D. J. L. G.: Antidepressant efficacy of high-frequency transcranial magnetic stimulation over the left dorsolateral prefrontal cortex in double-blind sham-controlled designs: a meta-analysis. Psychol. Med. 39, 65-75 (2009), Berlin;

(3) M. T., Van den Eynde, F. & Jeff Daskalakis, Z.: Clinically Meaningful Efficacy and Acceptability of Low-Frequency Repetitive Transcranial Magnetic Stimulation (rTMS) for Treating Primary Major Depression: A Meta-Analysis of Randomized, Double-Blind and Sham-Controlled Trials. Neuropsychopharmacology 38, 543-551 (2013);

(4) Smith, R., Allen, J. J., Thayer, J. F. & Lane, R. D.: Altered functional connectivity between medial prefrontal cortex and the inferior brainstem in major depression during appraisal of subjective emotional responses: A preliminary study. Biol. Psychol. 108, 13-24 (2015), and (5) Dua, S., & MacLean, P. D. Localization for Penile Erection in Medial Frontal Lobe. The American Journal of Physiology, 207, 1425-34, (1964).

Furthermore, reference is made to US2013/0085316 to Peter T. Fox and Jack L. Lancaster, describing apparatus and methods for computer-aided, robotic delivery of transcranial magnetic stimulation (TMS) using biologically derived feedback to establish coil position relative to brain functional regions. The apparatus includes a TMS coil mounted to a robotic member. The position of the stimulating coil can be automatically optimized using the TMS-induced bio-responses of various types.

In US2015/119689 to Alvaro Pascual-Leone and Michael D. Fox, describing techniques for identifying individual target sites for application of transcranial magnetic stimulation (TMS) to a brain of a patient for treatment of neurological and psychiatric disorders. The identification of the target TMS stimulation sites may be based on using functional connectivity magnetic resonance imaging (fMRI) to determine cortex regions of the brain that are functionally connected to other regions of the brain that may be stimulated to decrease symptoms of depression and other disorders. For example, target stimulation sites may be identified in the left dorsolateral prefrontal cortex (DLPFC) to remotely modulate the activity in a subgenual cingulate region and other limbic regions functionally connected with the DLPFC. TMS may be applied to the patient's head at the identified target TMS sites to treat depression and other neurological and psychiatric disorders.

SUMMARY OF THE INVENTION

A method is described whereby using electromagnetic stimulation, for instance via transcranial magnetic stimulation (TMS) puls(es), a correct cortical area (area 1) is identified, for instance allowing effective treatment or investigation of brain functioning.

The invention provides a method for identifying at least one cortical stimulation site in a subject for the application as a target that can be used for treatment of a psychiatric or neurological disorder related to a deep brain region of the ventromedial prefrontal cortex including the subgenual and rostral anterior cingulate by using a first focal-neuromodulation technique, said method comprising:
  applying pulses of a second a focal-neuromodulation technique to different cortical areas of said subject;
  simultaneously with the application of said pulses at a said cortical area measuring a psychophysiological signal representative of a heart rate of said subject for said cortical area, and
  when observing a systematic change in said psychophysiological signal, identifying a corresponding cortical area as said at least one cortical stimulation site that is functionally connected to said deep brain region of the ventromedial prefrontal cortex including the subgenual and rostral anterior cingulate for presenting said target for said treatment.

The invention further provides a system for identifying at least one cortical stimulation site in a subject for the application as a target that can be used for treatment of a psychiatric or neurological disorder related to a deep brain region of the ventromedial prefrontal cortex including the subgenual and rostral anterior cingulate by using a first focal-neuromodulation technique, said system comprising:
  a modulation device for applying pulses of a second a focal-neuromodulation technique to different cortical areas of said subject, said modulation device adapted for moving over a head of a subject at defined positions;
  a detector for measuring a psychophysiological signal representative of a heart rate of said subject for said cortical area simultaneously with the application of pulses at a said cortical area from said modulation device,
  said detector is functionally coupled to said modulation device for simultaneously measuring said psychophysiological signal while said modulation device applies said neuromodulation and
  said modulation device and said detector functionally coupled for on observation of a systematic change in said psychophysiological signal, identifying a position of a corresponding cortical area as said at least one cortical stimulation site that is functionally connected to said deep brain region of the ventromedial prefrontal cortex including the subgenual and rostral anterior cingulate for presenting said target for said treatment.

It was found that by measuring a psychophysiological signal that changes by manipulation of a deeper cortical or sub-cortical area (target area), i.e. trans-synaptical target identification, sites can be found that allow effective stimulation via electromagnetic stimulation or manipulation.

In particular, a method is described whereby using transcranial magnetic stimulation (TMS) puls(es) the correct cortical area (area 1) is identified by measuring a psychophysiological signal that changes by manipulation of a deeper cortical or sub-cortical area (target area), i.e. trans-synaptical target identification. In its preferred embodiment the invention entails the optimally and individualized targeting of the Ventromedial Prefrontal Cortex (VMPFC: including subgenual and rostral anterior cingulate)—which is to deep to directly target using TMS—by finding a site in the prefrontal cortex that results in a decreased heart-rate, as a result of trans-synaptic relay of the TMS signal from prefrontal cortex to VMPFC. The cortical area identified in this way is subsequently used for the therapeutic action of TMS in for example depression.

In an embodiment, in a closed-loop stimulation cycle a heart rate is measured in real time by means of ECG, an R-peak is determined in said ECG, a TMS pulse is triggered based upon said detection of said R-peak in real-time, a time is determined to a next R-peak, and a site having the largest latency between these subsequent R-peaks determines said cortical stimulation site.

In an embodiment, said first focal-neuromodulation technique comprises an electrical stimulation technique.

In an embodiment, said second focal-neuromodulation technique comprises an electrical stimulation technique.

In an embodiment, said at least one of said focal-neuromodulation technique comprises techniques applied at various frontal areas to stimulate or modulate underlying cortical tissue.

In an embodiment, said focal-neuromodulation technique is selected from transcranial direct current stimulation (tDCS), high-definition tDCS (HD-tDCS), transcranial alternating current stimulation (tACS), transcranial random noise stimulation (tRNS), Deep brain stimulation (DBS), ultrasound techniques, and a combination thereof.

In an embodiment, said first and second focal-neuromodulation technique are the same focal-neuromodulation technique.

In an embodiment, at least one of said first and second focal-neuromodulation technique comprises transcranial magnetic stimulation (TMS).

In an embodiment, the psychophysiological signal is selected from electrocardiogram (ECG), electromyogram (EMG), plethysmography, pupillometry, pneumograpy and combinations thereof.

In an embodiment, the systematic change is selected from distant effects, trans-synaptic effects, and a combination thereof.

In an embodiment, the TMS pulses are aimed at prefrontal areas to indirectly or trans-synaptically stimulate the Ventromedial Prefrontal Cortex, in particular including the rostral and subgenual anterior cingulate, identified by a decrease in heart rate during TMS stimulation trains.

In an embodiment, said method is optimized by using a concurrent task (either cognitive, physical or emotional) that increases basal heart-rate during concurrent with, or preceding the procedure.

In an embodiment, with the specific aim to enhance efficacy of antidepressant effects to rTMS.

The invention further relates to a use of the method to estimate the angular sensitivity of TMS stimulation, and to optimize the optimal angle of the rTMS coil for optimal stimulation.

In an embodiment of said use, said method is applied using various coil angles to identify the optimal coil-angle for stimulation.

In an embodiment, the method further comprises monitoring displacement of a stimulation coil during rTMS stimulation, wherein when the rTMS pulses no longer result in a change of said psychophysiological parameters, the stimulation coil and a persons head receiving said rTMS stimulation are displaced with respect to one another.

In an embodiment, said method comprises using a device for quantifying heart rate, in particular a device for generating an electrocardiogram (ECG) or plethsymography.

In an embodiment, said psychophysiological signal results from electromyography (EMG), galvanic skin response (GSR), electrodermal activity (EDA), pupillometry, pneumograpy or a combination thereof.

In an embodiment, said transcranial magnetic stimulation comprises applying trains of high frequency stimulation, in particular with a frequency larger than 1 Hz.

In an embodiment, said transcranial magnetic stimulation comprises applying trains of low frequency stimulation, in particular with a frequency slower than or equal to 1 Hz, or single pulses.

The invention further relates to a method for applying focal neuromodulation techniques to treat a psychiatric or neurological disorder, comprising identifying at least one cortical stimulation site in a subject for the application as a target to treat a psychiatric or neurological disorder related to a deep brain region of the ventromedial prefrontal cortex including the subgenual and rostral anterior cingulate according to the method of any one of the preceding claims, and subsequently applying said first/second focal neuromodulation technique to said identified cortical stimulation site.

In an embodiment, the treatment is applied while in a closed-loop stimulation cycle a heart rate is measured in real time by means of ECG, an R-peak is determined in said ECG, a TMS pulse is triggered based upon said detection of said R-peak in real-time, a time is determined to a next R-peak.

In an embodiment, the method is specifically applied to major depressive disorder (MDD) or depression.

wherein said detector is functionally coupled to said modulation device for simultaneously measuring said psychophysiological signal while said modulation device applies said neuromodulation, said system further comprising an actuator for displacing said modulation device over a head of said person while applying said focussed neuromodulation, and said detector is functionally coupled to said actuator for stopping displacement when a predetermined change of said psychophysiological signal occurs In an embodiment, the system further comprises an ECG device, functionally coupled to said modulation device for preforming in a closed-loop stimulation cycle a heart rate measurement in real time by means of ECG, determining an R-peak in said ECG, and triggering a TMS pulse by said modulation device based upon said detection of said R-peak in real-time, determining a time to a next R-peak, indicating a site having the largest latency between these subsequent R-peaks to determine said cortical stimulation site.

In an embodiment of the system for applying a focal-neuromodulation to a cortical area of a person, comprising:
  a modulation device for applying pulses of a second a focal-neuromodulation technique to a determined cortical area of said subject, said modulation device
  a detector for measuring a psychophysiological signal representative of a heart rate of said subject for said cortical area simultaneously with the application of pulses at a said cortical area from said modulation device, said detector is functionally coupled to said modulation device for simultaneously measuring said psychophysiological signal while said modulation device applies said neuromodulation and said modulation device and said detector functionally coupled for on observation of a systematic change in said psychophysiological signal, identifying a position of a corresponding cortical area as said at least one cortical stimulation site that is functionally connected to said deep brain region of the ventromedial prefrontal cortex including the subgenual and rostral anterior cingulate for presenting said target for said treatment.

In an embodiment, the system further comprises a computer system, functionally coupled to said modulation device, and to said detector, and comprising a computer program which, when running on said computer system, simultaneously controls said modulation device for applying a said pulse, and simultaneously controlling said detector for measuring said psychophysiological signal, and when a systematic change in said psychophysiological signal is determined, identifying a corresponding cortical area as said at least one cortical stimulation site that is functionally connected to said deep brain region of the ventromedial prefrontal cortex including the subgenual and rostral anterior cingulate for presenting said target for said treatment.

The invention further relates to a system for applying a focal-neuromodulation to a cortical area of a person, comprising:

the system for identifying at least one cortical stimulation site in a subject for the application as a target that can be used for treatment of a psychiatric or neurological disorder related to a deep brain region of the ventromedial prefrontal cortex including the subgenual and rostral anterior cingulate by using a first focal-neuromodulation technique, and further comprising a or said computer system, functionally coupled to said modulation device, and to said detector, and comprising a further computer program which, when running on said computer system, simultaneously controls said modulation device for applying a said pulse, and simultaneously controlling said detector for measuring said psychophysiological signal, and for monitoring said psychophysiological signal for monitoring said focussed neuromodulation of said cortical stimulation site.

In an embodiment at least one of said detector and said modulation device comprises an indicator for providing a sensory perceivable signal when a predetermined change of said psychophysiological signal occurs.

The invention further relates to a computer program which, when running on said computer system, simultaneously controls said modulation device for applying a said pulse, and simultaneously controlling said detector for measuring said psychophysiological signal, and when a systematic change in said psychophysiological signal is determined, identifying a corresponding cortical area as said at least one cortical stimulation site that is functionally connected to said deep brain region of the ventromedial prefrontal cortex including the subgenual and rostral anterior cingulate for presenting said target for said treatment.

In embodiments, the invention entails the optimally and individualized targeting of the Ventromedial Prefrontal Cortex (VMPFC: including subgenual and rostral anterior cingulate)—which is to deep to directly target using TMS—by finding a site in the prefrontal cortex that results in a decreased heart-rate, as a result by trans-synaptic relay of the TMS signal from prefrontal cortex to VMPFC. The cortical area identified in this way is subsequently used for the therapeutic action of TMS in for example depression. In an embodiment, transsynaptic relay can also comprise functional connectivity.

In this patent we will consistently speak about TMS as our preferred embodiment of the invention, however, this invention also applies to other focal-neuromodulation techniques including electrical stimulation techniques such as tDCS (transcranial direct current stimulation), tACS (transcranial alternating current stimulation), tRNS (transcranial random noise stimulation), DBS (Deep brain stimulation), ultrasound techniques etc.

TMS (transcranial magnetic stimulation) is a non-invasive neuromodulation technique with a direct influence on brain function. The basic principle of TMS is the application of short magnetic pulses over the scalp of a subject with the aim of inducing electrical currents in the neurons of the underlying—superficial—cortex, based on the principle of magnetic induction. The application of repetitive transcranial magnetic stimulation (rTMS) has been most well investigated in the treatment of major depressive disorder (MDD) or depression. Several meta-analyses have demonstrated that compared to placebo, the effects of rTMS applied to the left or right dorsolateral prefrontal cortex (DLPFC) have anti-depressant effects, see (1), (2), (3).

The right and left dorsolateral prefrontal cortex (DLPFC) have been the primary areas of interest for TMS stimulation in MDD. In most studies, localizing the DLPFC has been performed by means of the '5 cm rule' or sometimes a modified '6 cm rule'. The hand area of the primary motor cortex (M1) (which elicits a contralateral motor response of the thumb when stimulated), is taken as the detectable reference point on the scalp. From there, the coil is moved 5 or 6 cm anteriorly, in a sagittal direction. Another method for targeting the DLPFC is using the EEG 10-20 coordinate F3 or F4. Positioning the coil at these locations during treatment is assumed to target the DLPFC. However, it can be argued that these methods have limitations and may result in inconsistent and inaccurate targeting of the anatomically defined DLPFC. In order to solve this problem, technical advances such as structural MRI based neuronavigation systems have been developed and used. In neuronavigated rTMS, an MRI of a patient's brain is acquired before treatment, and the exact anatomical location of the DLPFC is established, relative to measurable anatomical landmarks of the skull such as nasion, inion, incisurae intertragicae etc. Combining this with software that can track a TMS coil in 3 dimensions, stimulation can be applied to an exact anatomically defined area. All these approaches 'assume' that the anatomical target—DLPFC—is the appropriate target mediating clinical efficacy in MDD. However, recent studies suggest that clinical efficacy of rTMS is more likely to be mediated by downstream (trans-synaptic) effects of rTMS in the ventromedial prefrontal cortex (more specifically: subgenual cingulate), and thus dependent on white matter projections—or other functional connectivity principles—from the DLPFC to this subgenual cingulate, see US2015/119689. These same authors have also proposed methods for optimizing cortical targeting of rTMS stimulation by brain imaging techniques such as MRI, and establishing the cortical area that demonstrates maximum anti-correlation with the subgenual cortex (suggestive of the fact that such areas are functionally connected) as a specific area to be targeted with rTMS, see US2015/119689. This approach differs from the above-mentioned approaches in that white matter connectivity is assumed to propagate the rTMS signal trans-synaptically to deeper cortical areas, opposed to the assumption that clinical effects are mediated at the superficial cortical level of the DLPFC. Still, these MRI targeted approaches require an individual MRI to be made and additional costly equipment, prohibiting widespread implementation of this TMS navigation method in clinical practice.

Assuming the aim of rTMS in depression is to indirectly achieve stimulation of the ventromedial prefrontal cortex (VMPFC)—which includes both the subgenual anterior cingulate (sgACC) and rostral anterior cingulate (rACC)—another approach to optimize individual cortical targets for rTMS, is to rely on functional anatomical knowledge of these areas. The VMPFC has been implicated in processing of emotional information and regulation of subsequent neural and visceral responses such as heart rate, for overview see (4).

In the same way as there is no more reliably way to localize the primary motor cortex area responsible for hand movement, by observing stimulation-induced hand movement (the basic method to establish a motor evoked potential or MEP), the same applies for other uses. Establishing an MEP is achieved by directly stimulating the primary motor cortex. However, the current invention specifically relates to distal (trans-synaptic) effects of stimulation. More specifically, the current invention proposes the use of directly observable bodily or psychophysiological measures such as heart rate (HR), sweat rate (GSR) etc. to in real-time individually target a desired cortical area by means of knowing the psychophysiological involvement of the areas such a cortical area projects to. Thereby, the current invention has the ability to precisely identify the correct area, rather then using guidance based on assumptions of a ⅝ cm. rule, F3 location or DLPFC area.

Prior studies have shown that direct electrical stimulation of VMPFC results in reduced heart rates, according to (5). However, the VMPFC is too deep to be reached by rTMS aimed at superficial cortical structures. Therefore, a specific embodiment of our invention implicates that measuring HR when firing a train of TMS pulses (for example 10 Hz, at for example 100% of the motor threshold) at various frontal areas, can help identify the area that is functionally connected to the VMPFC, and thus the best target for the treatment of MDD (in line with US2015/119689).

A difference between US2015/119689 and the current invention is the use of real-time psychophysiological measures (that index activity of the autonomic nervous system) used for targeting instead of using (offline) brain imaging markers.

Furthermore, one and the same equipment (TMS machine) can be used for both the localization method as well as the subsequent treatment with rTMS offering a more cost-effective solution. In the right and/or left frontal cortex of a human subject, TMS stimulation is applied at a grid consisting of various points surrounding the F3 or F4 position, for example separated by 1-2 cm., and the subsequent change in heart rate or heart rate variability (HRV) during and closely after a train of stimulation will be quantified in real-time, or heart-beat evoked potentials (HBEP) are generated from the ECG phase-locked to the TMS pulse. The stimulation site associated with the clearest change in HR, HRV or HBEP is then considered to be the optimum site for stimulation aimed at the VMPFC, and thus most effective site for treatment in depression.

Furthermore, a further improvement of the above procedure is by using a task (either cognitive, physical or emotional) that increases basal heart-rate and better quantify the changes, especially decreases in heart rate. Different frequencies of TMS trains (e.g. 9.5 Hz, 2 Hz, 40 Hz or patterned TMS such as theta burst stimulation) could possibly have different effects, where one frequency could increase and another frequency can decrease heart rate or HRV.

Finally, the current invention can also be used as a real-time method to assess if the stimulation coil is still across the right cortical site, by real-time inspection of heart rate while a patient is undergoing therapeutically rTMS at the using this method established site, since when the patient or the coil moves during a session no changes in heart rate or HRV are seen anymore, ensuring real-time verification of stimulation accuracy. This method is named: Neuro-Cardiac-Guided rTMS or NCG-rTMS.

The invention further relates to a method of identifying and guiding cortical stimulation sites for the application of a focal-neuromodulation techniques in a patient, which method comprises:
  applying TMS pulses to different cortical areas,
  simultaneously measuring a psychophysiological signal,
  observing a systematic change in the psychophysiological signal, as a result of stimulation of one or more specific cortical areas where the systematic change can only be the result of that cortical area being functionally connected to that area, and
  using at least one of these sites as the target for applying focal neuromodulation techniques to treat a psychiatric or neurological disorder.

The invention further relates to a system for applying a focal-neuromodulation to a cortical area of a person, comprising:
  a modulation device for applying a focussed neuromodulation to a cortical area of a person,
  an actuator for displacing said modulation device over a head of said person while applying said focussed neuromodulation, and
  a detector for measuring a psychophysiological signal,
  wherein said detector is functionally coupled to said modulation device for simultaneously measuring said psychophysiological signal while said modulation device applies said neuromodulation, and said detector is functionally coupled to said actuator for stopping displacement when a predetermined change of said psychophysiological signal occurs.

The invention further relates to a system for applying a focal-neuromodulation to a cortical area of a person, comprising:
  a modulation device for applying a focussed neuromodulation to a cortical area of a person, and
  a detector for measuring a psychophysiological signal,
  wherein said detector is functionally coupled to said modulation device for simultaneously measuring said psychophysiological signal while said modulation detector applies said neuromodulation, and at least one of said detector and said modulation device comprises an indicator for providing a sensory perceivable signal when a predetermined change of said psychophysiological signal occurs.

The person skilled in the art will understand the term "substantially" in this application, such as in "substantially encloses" or in "substantially extends up to". The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

Furthermore, the terms first, second, third and the like if used in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The construction elements herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawing in which corresponding reference symbols indicate corresponding parts, showing in FIG. 1 an embodiment of a system.

The drawings are not necessarily on scale.

DESCRIPTION OF PREFERRED EMBODIMENT

In FIG. 1, an embodiment of the system for applying a focal-neuromodulation to a cortical area of a person 1 is depicted. In this embodiment, the system comprises a modulation device 2 for applying a focussed neuromodulation to a cortical area of the person 1. The modulation device 2 has a modulation signal sender head 3. The modulation signal sender head 3 in this embodiment sends magnetic pulses that are focused at a particular point away from the sender 3, here at a position in the head of persons 1. Here, the sender head 3 is moved over the persons head by hand. Alternatively, it may be attached to or incorporated into an actuator for displacing said modulation device 2 or, in the current embodiment for instance the sender head 3, over a head of said person while applying said focussed neuromodulation. The person 1 is further provided with a detector 4 for measuring a psychophysiological signal. In this embodiment of FIG. 1, the detector 4 comprises a heartrate monitor. The detector 4 in this embodiment is provided with a computer program for processing the psychophysiological signal and for determining if and when a predetermined change of said psychophysiological signal occurs. In an embodiment, the detector 4 and/or the modulation device 2 can be provided with a signaller for providing a sensory perceivable signal when a predetermined change of said psychophysiological signal occurs. The detector 2 and the modulation device 2 may be functionally coupled, for instance via a wire or wirelessly. In an embodiment, as explained, the detector 2 and/or the modulation device 2 and/or the sender head 3 may be functionally coupled to an actuator for moving the part that sends the pulses over the head of the person 1. When software running on said detector 4 and/or the modulation device 2 determines predetermined change of said psychophysiological signal, the actuator stops and treatment can start. In this embodiment, the first and second focal-neuromodulation technique are the same.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

The invention claimed is:

1. A method for identifying at least one cortical stimulation site in a subject for the application as a target that can be used for treatment of a psychiatric or neurological disorder related to a deep brain region of the ventromedial prefrontal cortex including the subgenual and rostral anterior cingulate by using a first focal-neuromodulation technique, said method comprising:
    applying pulses of a second a focal-neuromodulation technique to different cortical areas of said subject;
    simultaneously with the application of said pulses at a said cortical area measuring a psychophysiological signal representative of a heart rate of said subject for said cortical area, and
    when observing a systematic change in said psychophysiological signal indicating a decrease in heart rate, identifying a corresponding cortical area as said at least one cortical stimulation site that is functionally connected to said deep brain region of the ventromedial prefrontal cortex including the subgenual and rostral anterior cingulate for presenting said target for said treatment.

2. The method of claim 1, wherein in a closed-loop stimulation cycle a heart rate is measured in real time by means of ECG, an R-peak is determined in said ECG, a TMS pulse is triggered based upon said detection of said R-peak in real-time, a time is determined to a next R-peak, and a site having the largest latency between these subsequent R-peaks determines said cortical stimulation site.

3. The method of claim 2, wherein the TMS pulses are aimed at prefrontal areas to indirectly or trans-synaptically stimulate the Ventromedial Prefrontal Cortex, in particular including the rostral and subgenual anterior cingulate, identified by a decrease in heart rate during TMS stimulation trains.

4. The method of claim 1, wherein said first focal-neuromodulation technique comprises an electrical stimulation technique.

5. The method of claim 1, wherein said second focal-neuromodulation technique comprises an electrical stimulation technique.

6. The method of claim 1, wherein said at least one of said focal-neuromodulation technique comprises techniques applied at various frontal areas to stimulate or modulate underlying cortical tissue.

7. The method of claim 6, wherein said focal-neuromodulation technique is selected from transcranial direct current stimulation (tDCS), high-definition tDCS (HD-tDCS), transcranial alternating current stimulation (tACS), transcranial random noise stimulation (tRNS), Deep brain stimulation (DBS), ultrasound techniques, and a combination thereof.

8. The method of claim 1, wherein said first and second focal-neuromodulation technique are the same focal-neuromodulation technique.

9. The method of claim 1, wherein at least one of said first and second focal-neuromodulation technique comprises transcranial magnetic stimulation (TMS).

10. The method of claim 9, wherein said transcranial magnetic stimulation comprises applying trains of high frequency stimulation, in particular with a frequency larger than 1 Hz.

11. The method of claim 9, wherein said transcranial magnetic stimulation comprises applying trains of low frequency stimulation, in particular with a frequency slower than or equal to 1 Hz, or single pulses.

12. The method of claim 1, wherein the psychophysiological signal is selected from electrocardiogram (ECG), electromyogram (EMG), plethysmography, pupillometry, pneumograpy and combinations thereof.

13. The method of claim 1, wherein the systematic change is selected from distant effects, trans-synaptic effects, and a combination thereof.

14. The method of claim 1, wherein said method is optimized by using a concurrent task (either cognitive, physical or emotional) that increases basal heart-rate during concurrent with, or preceding the procedure.

15. The method of claim 1, with the specific aim to enhance efficacy of antidepressant effects to rTMS.

16. The use of claim 15 wherein said method is applied using various coil angles to identify the optimal coil-angle for stimulation.

17. Use of the method of claim 1 to estimate the angular sensitivity of TMS stimulation, and to optimize the optimal angle of the rTMS coil for optimal stimulation.

18. The method of claim 1, further comprising monitoring displacement of a stimulation coil during rTMS stimulation, wherein when the rTMS pulses no longer result in a change of said psychophysiological parameters, the stimulation coil and a person's head receiving said rTMS stimulation are displaced with respect to one another.

19. The method of claim 1, wherein said method comprises using a device for quantifying heart rate, in particular a device for generating an electrocardiogram (ECG) or plethsymography.

20. The method of claim 1, wherein said psychophysiological signal results from electromyography (EMG), galvanic skin response (GSR), electrodermal activity (EDA), pupillometry, pneumograpy or a combination thereof.

21. A method for applying focal neuromodulation techniques to treat a psychiatric or neurological disorder, comprising identifying at least one cortical stimulation site in a subject for the application as a target to treat a psychiatric or neurological disorder related to a deep brain region of the ventromedial prefrontal cortex including the subgenual and rostral anterior cingulate according to the method of claim 1, and subsequently applying said first/second focal neuromodulation technique to said identified cortical stimulation site.

22. The method of claim 1, wherein said treatment is applied while in a closed-loop stimulation cycle a heart rate is measured in real time by means of ECG, an R-peak is determined in said ECG, a TMS pulse is triggered based upon said detection of said R-peak in real-time, a time is determined to a next R-peak.

23. The method of claim 21, specifically applied to major depressive disorder (MDD) or depression.

24. A system for identifying at least one cortical stimulation site in a subject for the application as a target that can be used for treatment of a psychiatric or neurological disorder related to a deep brain region of the ventromedial prefrontal cortex including the subgenual and rostral anterior cingulate by using a first focal-neuromodulation technique, said system comprising:
   a modulation device for applying pulses of a second a focal-neuromodulation technique to different cortical areas of said subject, said modulation device adapted for moving over a head of a subject at defined positions;
   a detector for measuring a psychophysiological signal representative of a heart rate of said subject for said cortical area simultaneously with the application of pulses at a said cortical area from said modulation device;
   said detector is functionally coupled to said modulation device for simultaneously measuring said psychophysiological signal while said modulation device applies said pulses and
   said modulation device and said detector functionally coupled for on observation of a systematic change in said psychophysiological signal indicating a decrease in heart rate, identifying a position of a corresponding cortical area as said at least one cortical stimulation site that is functionally connected to said deep brain region of the ventromedial prefrontal cortex including the subgenual and rostral anterior cingulate for presenting said target for said treatment.

25. The system of claim 24, wherein said detector is functionally coupled to said modulation device for simultaneously measuring said psychophysiological signal while said modulation device applies said neuromodulation, said system further comprising an actuator for displacing said modulation device over a head of said person while applying said focused neuromodulation, and
   said detector is functionally coupled to said actuator for stopping displacement when a predetermined change of said psychophysiological signal occurs.

26. The system of claim 24, further comprising an ECG device functionally coupled to said modulation device for preforming in a closed-loop stimulation cycle a heart rate measurement in real time by means of ECG, determining an R-peak in said ECG, and triggering a TMS pulse by said modulation device based upon said detection of said R-peak in real-time, determining a time to a next R-peak, indicating a site having the largest latency between these subsequent R-peaks to determine said cortical stimulation site.

27. The system of claim 26 for applying a focal-neuromodulation to a cortical area of a person for treatment, said system comprising:

a modulation device for applying pulses of a second a focal-neuromodulation technique to a determined cortical area of said subject;

a detector for measuring a psychophysiological signal representative of a heart rate of said subject for said cortical area simultaneously with the application of pulses at a said cortical area from said modulation device;

said detector is functionally coupled to said modulation device for simultaneously measuring said psychophysiological signal while said modulation device applies said pulses and said modulation device and said detector functionally coupled for on observation of a systematic change in said psychophysiological signal, identifying a position of a corresponding cortical area as said at least one cortical stimulation site that is functionally connected to said deep brain region of the ventromedial prefrontal cortex including the subgenual and rostral anterior cingulate for presenting said target for said treatment.

28. The system of claim 24, further comprising a computer system, functionally coupled to said modulation device, to said detector, and comprising a computer program which, when running on said computer system, simultaneously controls said modulation device for applying a said pulse, and simultaneously controls said detector for measuring said psychophysiological signal, and when a systematic change in said psychophysiological signal is determined, identifying a corresponding cortical area as said at least one cortical stimulation site that is functionally connected to said deep brain region of the ventromedial prefrontal cortex including the subgenual and rostral anterior cingulate for presenting said target for said treatment.

29. A system for applying a focal-neuromodulation to a cortical area of a person, comprising:

the system according to claim 24 for identifying at least one cortical stimulation site in a subject for the application as a target that can be used for treatment of a psychiatric or neurological disorder related to a deep brain region of the ventromedial prefrontal cortex including the subgenual and rostral anterior cingulate by using a first focal-neuromodulation technique, and further comprising a or said computer system, functionally coupled to said modulation device, and to said detector, and comprising a further computer program which, when running on said computer system, simultaneously controls said modulation device for applying a said pulse, and simultaneously controlling said detector for measuring said psychophysiological signal, and monitoring said psychophysiological signal for monitoring said focused neuromodulation of said cortical stimulation site.

30. The system of claim 24, wherein at least one of said detector and said modulation device comprises an indicator for providing a sensory perceivable signal when a predetermined change of said psychophysiological signal occurs.

* * * * *